US009713661B2

(12) United States Patent
Coston et al.

(10) Patent No.: US 9,713,661 B2
(45) Date of Patent: Jul. 25, 2017

(54) BIOLOGICAL FLUID COLLECTION SYSTEM

(75) Inventors: Anthony F. Coston, Lawrenceville, GA (US); Paul Ciccone, Social Circle, GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 1199 days.

(21) Appl. No.: 13/516,601

(22) PCT Filed: Dec. 21, 2010

(86) PCT No.: PCT/US2010/061600
§ 371 (c)(1),
(2), (4) Date: Sep. 4, 2012

(87) PCT Pub. No.: WO2011/079132
PCT Pub. Date: Jun. 30, 2011

(65) Prior Publication Data
US 2012/0323144 A1    Dec. 20, 2012

Related U.S. Application Data

(60) Provisional application No. 61/289,869, filed on Dec. 23, 2009.

(51) Int. Cl.
*A61M 1/00*    (2006.01)
(52) U.S. Cl.
CPC ........ *A61M 1/0066* (2013.01); *A61M 1/0072* (2014.02); *A61M 2202/0496* (2013.01); *A61M 2210/1085* (2013.01)

(58) Field of Classification Search
USPC ......................................................... 604/317
See application file for complete search history.

(56) References Cited

U.S. PATENT DOCUMENTS

| | | | |
|---|---|---|---|
| 3,961,529 A | 6/1976 | Hanifl | |
| 4,227,533 A | 10/1980 | Godfrey | |
| 4,423,741 A | 1/1984 | Levy | |
| 4,445,889 A * | 5/1984 | Wong | A61M 1/0096 604/317 |
| 4,819,653 A | 4/1989 | Marks | |

(Continued)

OTHER PUBLICATIONS

PCT/US2010/061600 filed Dec. 21, 2010 International Preliminary Report on Patentability dated Jun. 26, 2012 and Written Opinion dated Feb. 28, 2011.

(Continued)

*Primary Examiner* — Tatyana Zalukaeva
*Assistant Examiner* — Guy K Townsend
(74) *Attorney, Agent, or Firm* — Rutan & Tucker, LLP

(57) ABSTRACT

A drainage and/or collection system (1) for biological fluids includes at least one conduit (40) for transporting a biological fluid (F) from a catheter (10) to a collection device (50) and a gas pressure source (70) configured to feed a gas (G) into the at least one conduit (40) between the catheter (10) and the collection device (50). The gas (G) causes the biological fluid (F) arranged in the at least one conduit (40) to drain into the collection device (50). A method includes inserting a catheter (10), draining a fluid (F) into a collection device (50) via a conduit (40), and introducing gas (G) into the conduit (40) so as to force fluid (F) remaining in the conduit (40) into the collection device (50).

18 Claims, 11 Drawing Sheets

(56) References Cited

U.S. PATENT DOCUMENTS

| | | | |
|---|---|---|---|
| 6,240,960 B1 | 6/2001 | Fillmore | |
| 6,338,728 B1* | 1/2002 | Valerio | A61M 1/0013 604/317 |
| 6,481,462 B2 | 11/2002 | Fillmore et al. | |
| 6,749,592 B2* | 6/2004 | Lord | G05D 16/0655 604/317 |
| 7,361,184 B2* | 4/2008 | Joshi | A61M 1/0066 602/42 |
| 7,998,125 B2* | 8/2011 | Weston | A61M 1/008 52/2.18 |
| 2005/0203452 A1* | 9/2005 | Weston | A61M 1/0088 602/13 |
| 2005/0222527 A1* | 10/2005 | Miller | A61M 1/0088 602/1 |
| 2007/0010797 A1 | 1/2007 | Nishtala et al. | |
| 2007/0010798 A1 | 1/2007 | Stoller et al. | |
| 2007/0021713 A1* | 1/2007 | Kumar | A61M 3/0258 604/27 |
| 2007/0118096 A1* | 5/2007 | Smith | A61B 5/445 604/541 |
| 2007/0161949 A1 | 7/2007 | Knox et al. | |
| 2007/0265585 A1* | 11/2007 | Joshi | A61M 1/0088 604/313 |
| 2007/0265586 A1* | 11/2007 | Joshi | A61M 1/0031 604/313 |
| 2008/0114338 A1 | 5/2008 | Kumar | |
| 2009/0005746 A1* | 1/2009 | Nielsen | A61M 1/0031 604/315 |
| 2009/0012484 A1* | 1/2009 | Nielsen | A61M 1/0031 604/319 |
| 2009/0036873 A1* | 2/2009 | Nielsen | A61M 1/0031 604/543 |
| 2009/0281526 A1* | 11/2009 | Kenny | A61M 1/0088 604/543 |
| 2009/0306609 A1* | 12/2009 | Blott | A61M 1/0037 604/305 |
| 2010/0042074 A1* | 2/2010 | Weston | A61M 1/0066 604/543 |
| 2010/0137775 A1* | 6/2010 | Hu | A61M 1/0088 602/54 |
| 2010/0150991 A1* | 6/2010 | Bernstein | A61K 31/00 424/447 |
| 2010/0262126 A1* | 10/2010 | Hu | A61M 1/0088 604/543 |
| 2011/0009838 A1* | 1/2011 | Greener | A61M 1/0088 604/319 |
| 2011/0130712 A1* | 6/2011 | Topaz | A61M 1/0084 604/23 |
| 2012/0323144 A1* | 12/2012 | Coston | A61M 1/0066 600/581 |
| 2013/0218106 A1* | 8/2013 | Coston | A61B 5/207 604/317 |
| 2013/0296816 A1* | 11/2013 | Greener | A61M 1/0031 604/320 |

OTHER PUBLICATIONS

PCT/US2010/061600 filed Dec. 21, 2010 International Search Report dated Feb. 28, 2011.

\* cited by examiner

BIOLOGICAL FLUID COLLECTION SYSTEM

CROSS REFERENCE TO RELATED APPLICATIONS

This application is a U.S. national stage application under 35 USC §371 of International Application No. PCT/US2010/061600, filed Dec. 21, 2010, claiming priority to U.S. Provisional Patent Application No. 61/289,869, filed Dec. 23, 2009, each of which is incorporated by reference in its entirety into this application.

BACKGROUND OF THE INVENTION

Catheterization is a sterile process of draining urine from the bladder. Typically, a catheter is inserted into a bladder so that fluid can pass out through the catheter, into a conduit and then into a collection vessel. The amount of urine in the collection vessel is then measured.

With known systems, a significant amount of urine can remain or pool in the conduit and does not easily pass into the collection vessel. As such, it is difficult to determine accurately how much urine actually exited from the bladder. Urine output readings can thus not be accurately determined this way.

While it is possible manipulate or move (or "milk") the conduit so that some urine trapped in the conduit can be forced or flushed via gravity into the collection vessel, this method is limited by things such as the following; because of limited venting, it is difficult to remove all of most of the urine in the conduit; and some urine will necessarily adhere to the inner wall of the conduit owing to factors such as surface tension. Also, this pooling of fluid within the conduit typically forces a clinician to intervene in order to force fluid into the collection vessel.

What is needed is a more reliable, consistent and easier way to accurately collect a biological fluid such as urine. What is needed is a system and method wherein a substantial portion of the fluid trapped in a fluid removal conduit is forced into the collection vessel using a gas in order to more accurately determine a quantity or volume of removed fluid. What is needed is a system and method which can more reliably and easily be used to accurately collect a fluid such as urine from a user. What is also needed is a system that reduces or eliminates the need for user intervention.

SUMMARY OF THE INVENTION

According to one non-limiting embodiment of the invention, there is provided a drainage system for biological fluids which comprises at least one conduit for transporting a biological fluid from a catheter to a collection device and a gas pressure source configured to feed a gas into the at least one conduit between the catheter and the collection device. The gas causes the biological fluid arranged in the at least one conduit to drain into the collection device.

According to one non-limiting embodiment of the invention, there is provided a drainage and/or collection system for biological fluids which comprises at least one conduit for transporting a biological fluid from a catheter to a collection device and a gas pressure source configured to feed a gas into the at least one conduit between the catheter and the collection device. The gas causes the biological fluid arranged in the at least one conduit to drain into the collection device.

In embodiments, a pressure of the gas exiting the gas pressure source is at least greater than atmospheric pressure and having the form of a single pressure pulse, greater than atmospheric pressure and having the form of a gas flow which occurs for a predetermined amount of time, greater than atmospheric pressure and having the form of a gas flow which occurs for between about 1 second and about 10 seconds, greater than atmospheric pressure and having the form of a single pressure pulse, and sufficiently high so as to cause substantially all fluid in the at least one conduit to drain into the collection device.

In embodiments, the gas pressure source is manually actuated device. In embodiments, the gas pressure source is one of a bulb syringe and a squeeze bulb.

In embodiments, the drainage system further comprises a device preventing fluid movement between the gas pressure source and the catheter. In embodiments, the device is a one-way valve coupled to the at least one conduit. In embodiments, the device is arranged closer to the catheter than to the collection device. In embodiments, the device has one end in fluid communication with the catheter and another end in fluid communication with the collection device. In embodiments, the device has one end in fluid communication with the catheter and another end in fluid communication with the gas pressure source and the collection device. In embodiments, the device at least one access port for removing a sample of the biological fluid passing from the catheter to the collection device. In embodiments, at least one access port for removing a sample of the biological fluid is arranged at a point upstream of the device. In embodiments, at least one access port is coupled to the at least one conduit for removing a sample of the biological fluid passing from the catheter and through the at least one conduit.

In embodiments, the system has the following modes of operation; a first mode wherein the biological fluid passes from the catheter through the at least one conduit and into collection device, and a second mode wherein the gas passes from the gas pressure source into the at least one conduit and into collection device.

In embodiments, the system has the following modes of operation; a collection mode wherein the biological fluid passes from the catheter through the at least one conduit and into collection device, and a draining mode wherein the gas passes from the gas pressure source into the at least one conduit and causes a substantial portion of the biological fluid remaining in the least one conduit after the collection mode to drain into collection device.

In embodiments, the system has the following modes of operation; a collection mode wherein the biological fluid passes from the catheter through the at least one conduit and into collection device substantially until at least one of the biological fluid stops passing into the collection device and a least a predetermined amount of time has expired, a draining mode wherein the gas passes from the gas pressure source into the at least one conduit and causes a substantial portion of the biological fluid remaining in the least one conduit after the collection mode to drain into collection device. In the draining mode, the gas is prevented from passing into the catheter or bladder.

In embodiments, the drainage system further comprises a housing configured to at least partially enclose at least one of a device preventing fluid movement between the gas pressure source and the catheter and a device preventing fluid movement between the at least one conduit and the gas pressure source.

In embodiments, the drainage system further comprises a housing configured to at least partially enclose at least one of a one-way valve preventing fluid movement between the pressure source and the catheter and allowing fluid movement between the catheter and the collection device and a one-way valve preventing fluid movement between the at least one conduit and the gas pressure source and allowing gas movement between the gas pressure source and the collection device.

In embodiments, the drainage system further comprises a control device having at least two ports in fluid communication with the at least one conduit and containing therein at least one of a device preventing fluid movement between the gas pressure source and the catheter and a device preventing fluid movement between the at least one conduit and the gas pressure source.

In embodiments, the control device has the following modes of operation; a first mode wherein the biological fluid passes from the catheter through the at least one conduit and into collection device, and a second mode wherein the biological fluid is prevented from passing from the catheter to the collection device and the gas passes from the gas pressure source into the at least one conduit and into collection device. In embodiments, the control device comprises at least one access port for removing a sample of the biological fluid.

In embodiments, the control device further comprises a mechanical switch having the following modes of operation; a first mode wherein the biological fluid passes from the catheter through the at least one conduit and into collection device, and a second mode wherein the biological fluid is prevented from passing from the catheter to the collection device and the gas passes from the gas pressure source into the at least one conduit and into collection device.

In embodiments, the drainage system further comprises a control device comprising a first port in fluid communication with the catheter, a second port in fluid communication with the collection device, a third port in fluid communication with the gas pressure source, a sampling port for removing a sample of the biological fluid, and at least one of a device preventing fluid movement between the gas pressure source and the catheter and a device preventing fluid movement between the at least one conduit and the gas pressure source.

In embodiments, the drainage system further comprises a control device comprising a first port in fluid communication with the catheter, a second port in fluid communication with the collection device, a third port in fluid communication with the gas pressure source, and at least one of a one-way valve preventing fluid movement between the gas pressure source and the catheter and allowing fluid movement between the catheter and the collection device and a one-way valve preventing fluid movement between the at least one conduit and the gas pressure source and allowing gas movement between the gas pressure source and the collection device.

In embodiments, the gas pressure source comprises a device for storing the gas and a device for switching on the gas. In embodiments, the gas pressure source comprises a device supplying the gas and a device for switching on the gas. In embodiments, the gas pressure source comprises a gas supply and a gas regulating device having the following modes of operation; a first position wherein the gas is fed into the at least one conduit from the gas supply, and a second position wherein the gas is prevented from passing into the at least one conduit. In embodiments, the gas regulating device is a mechanically actuated gas regulating device. In embodiments, the gas regulating device has one end in fluid communication with a conduit that is coupled to the gas supply and another end in fluid communication with the at least one conduit. In embodiments, the gas regulating device comprises a device preventing fluid movement between the at least one conduit and the gas supply.

In embodiments, the collection device may comprise at least one of; indicia indicating a quantity of the biological fluid disposed within the collection device, a device for venting the gas entering the collection device, a device providing an indication that a draining of the conduit is substantially complete, a device or hydrophilic filter for allowing gas to exit the collection device and prevent fluid from exiting the collection chamber, and a device for venting the gas entering the collection device so that a pressure in the collection chamber is substantially maintained at that of the atmosphere outside of the collection chamber.

In embodiments, the catheter is a Foley catheter and the biological fluid is urine.

According to one non-limiting embodiment of the invention, there is provided a system for draining a bladder. The system comprises a catheter for insertion into said bladder and a drainage system having one or more of the features described above.

In embodiments, the catheter is a Foley catheter. In embodiments, the catheter is a Jackson Pratt tube. In embodiments, the collection device is a drainage bag. In embodiments, the collection device comprises an anti-reflux trap. In embodiments, the trap is separate or separable from the collection device. In embodiments, the system is a closed system.

According to one non-limiting embodiment of the invention, there is provided a method of draining fluid using one or more features described above, wherein the method comprises inserting a catheter, draining a fluid into a collection device via a conduit, and introducing gas into the conduit so as to force fluid remaining in the conduit into the collection device.

In embodiments, the method may further comprise preventing the gas from entering the user and/or patient. In embodiments, the introducing occurs after the draining.

According to one non-limiting embodiment of the invention, there is provided a method of draining urine using one or more features described above, wherein the method comprises inserting a catheter into a bladder, draining urine into a collection device from the catheter, and introducing gas into a conduit used to pass urine into the collection device.

In embodiments, the method may further comprise preventing the gas from entering the bladder. In embodiments, the method comprises, after the draining, removing with the gas a substantial portion of the fluid remaining in the conduit.

In embodiments, the system and method is utilized on a collection system of the type disclosed in US 2007/0010797 to NISHTALA et al., the disclosure of this document is expressly incorporated by reference herein in its entirety.

In embodiments, the system and method is utilized on a collection system of the type disclosed in U.S. Pat. No. 3,961,529 to HANIFL, the disclosure of this document is expressly incorporated by reference herein in its entirety.

In embodiments, the system and method utilizes a sampling coupling device of the type disclosed in U.S. Pat. No. 4,423,741 to LEVY, the disclosure of this document is expressly incorporated by reference herein in its entirety.

In embodiments, the system and method utilizes on a communication control system of the type disclosed in U.S.

Pat. No. 4,819,653 to MARKS, the disclosure of this document is expressly incorporated by reference herein in its entirety.

In embodiments, the system and method utilizes a catheter of the type disclosed in U.S. Pat. No. 4,227,533 to GODFREY, the disclosure of this document is expressly incorporated by reference herein in its entirety.

In embodiments, the system and method utilizes one or more one-way valves of the type disclosed in U.S. Pat. No. 6,240,960 to FILLMORE and U.S. Pat. No. 6,481,462 to FILLMORE et al., the disclosures of this document are each expressly incorporated by reference herein in their entireties.

BRIEF DESCRIPTION OF DRAWINGS OF THE EXEMPLARY EMBODIMENTS

DETAILED DESCRIPTION OF THE EXEMPLARY EMBODIMENTS

The following description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will enable one skilled in the art to make and use the invention, and describes several embodiments, adaptations, variations, alternatives and uses of the invention, including what is presently believed to be the best mode of carrying out the invention.

As used herein, the reference terms "proximal" and "distal" (proximal being closer than distal) refer to proximity with respect to a health care professional catheterizing a patient. For example, the region or section of the catheter apparatus that is closest to the health care professional during catheterization is referred to herein as "proximal," while a region or section of the catheter apparatus closest to the patient's bladder is referred to as "distal." In the case of a self-catheterizing patient, proximal refers to a point external to the patient's body, and distal refers to a point within the patient's body (i.e., the bladder).

The catheter draining system as described herein is discussed in the context of a urinary catheter for insertion into a bladder for drainage of urine therefrom. The instant system, however, may also be used for other applications not specifically mentioned herein. As such, the instant invention is not limited to urinary catheter applications.

Figure 1:
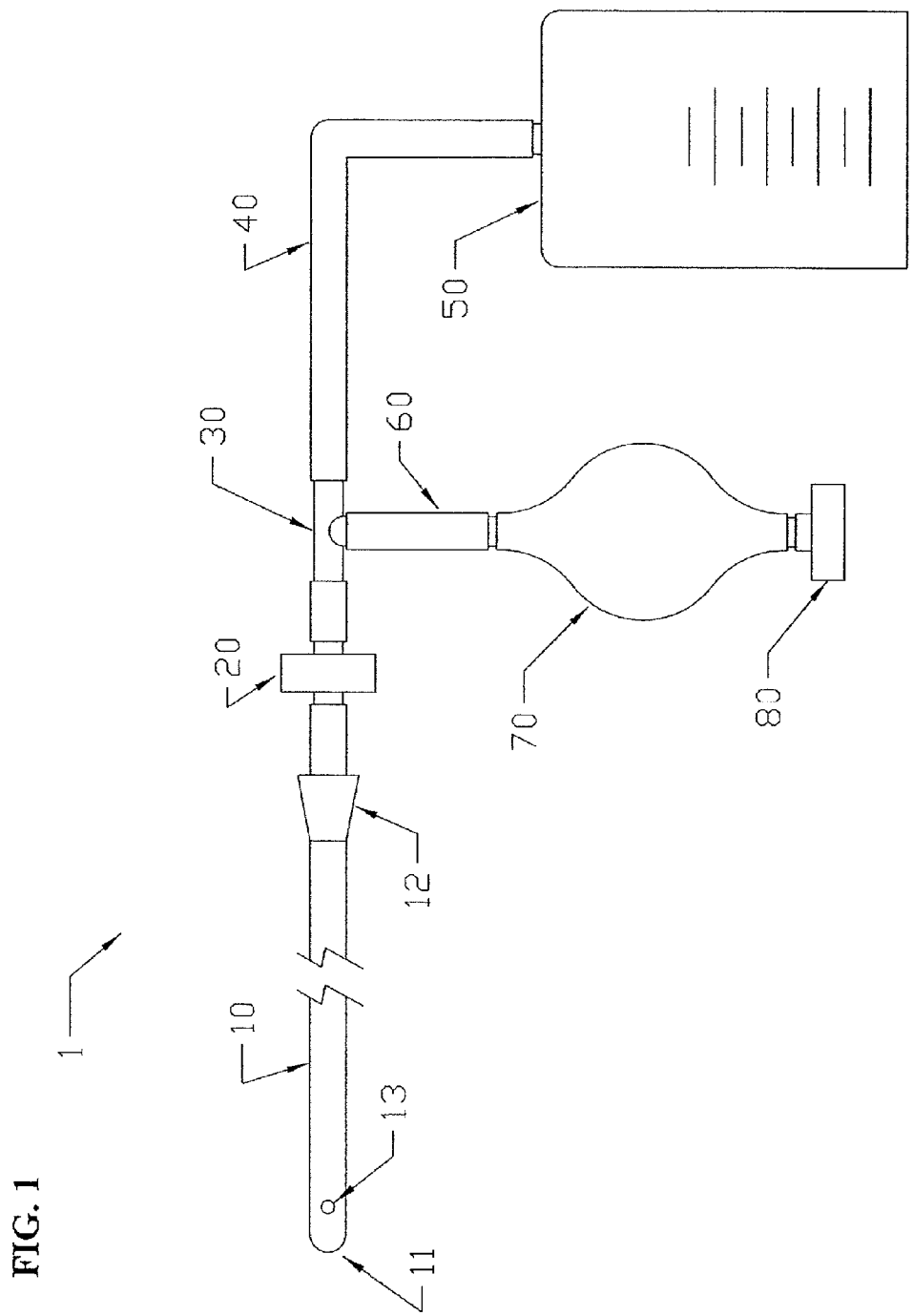
FIG. 1 shows a system for draining and flushing a biological fluid in accordance with one non-limiting embodiment of the invention.
Figure 2:
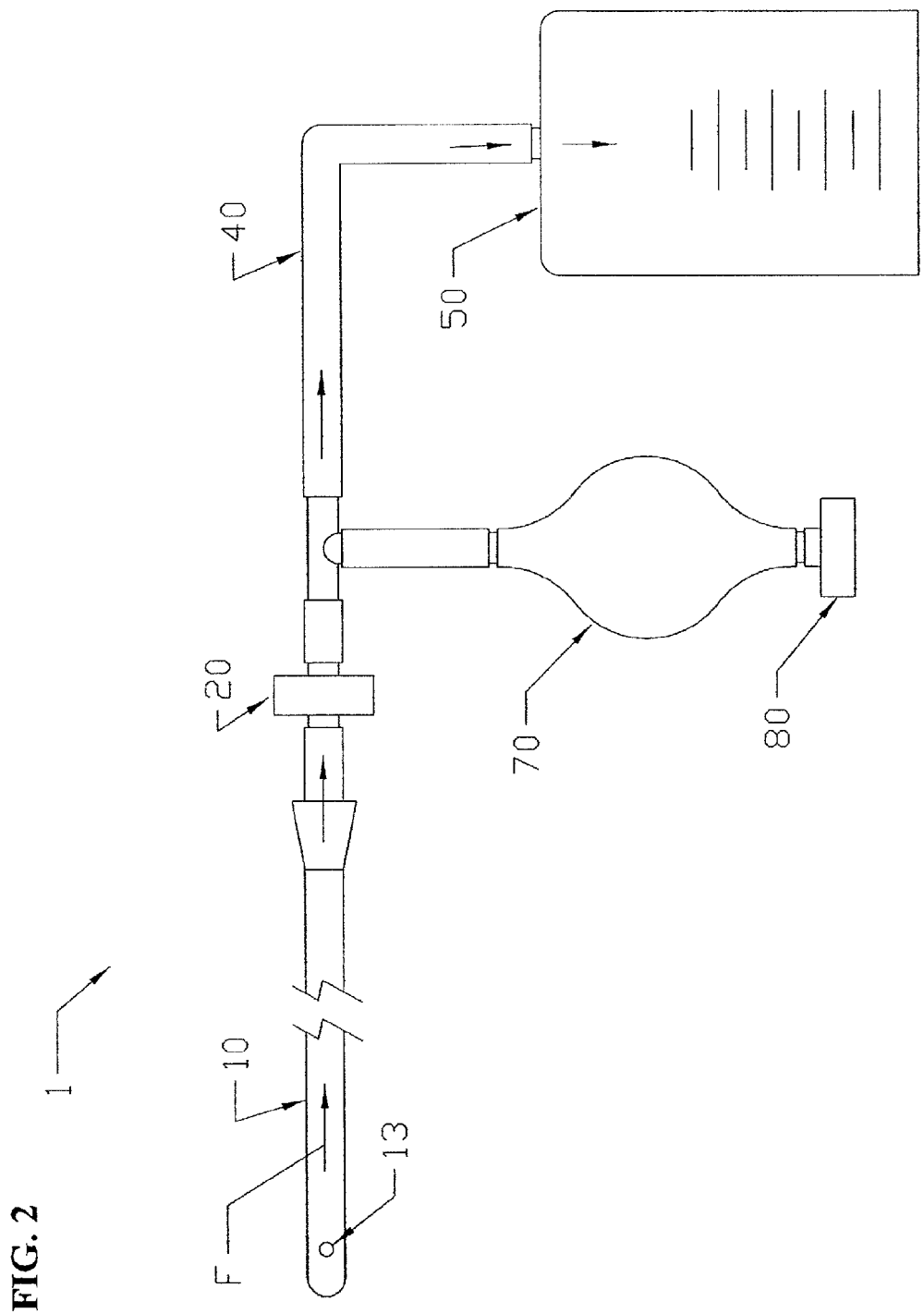
FIG. 2 shows the system of FIG. 1 during a draining operation mode in accordance with one non-limiting aspect of the invention and shows fluid passing out of a catheter, thought a conduit and into a collection vessel.
Figure 3:
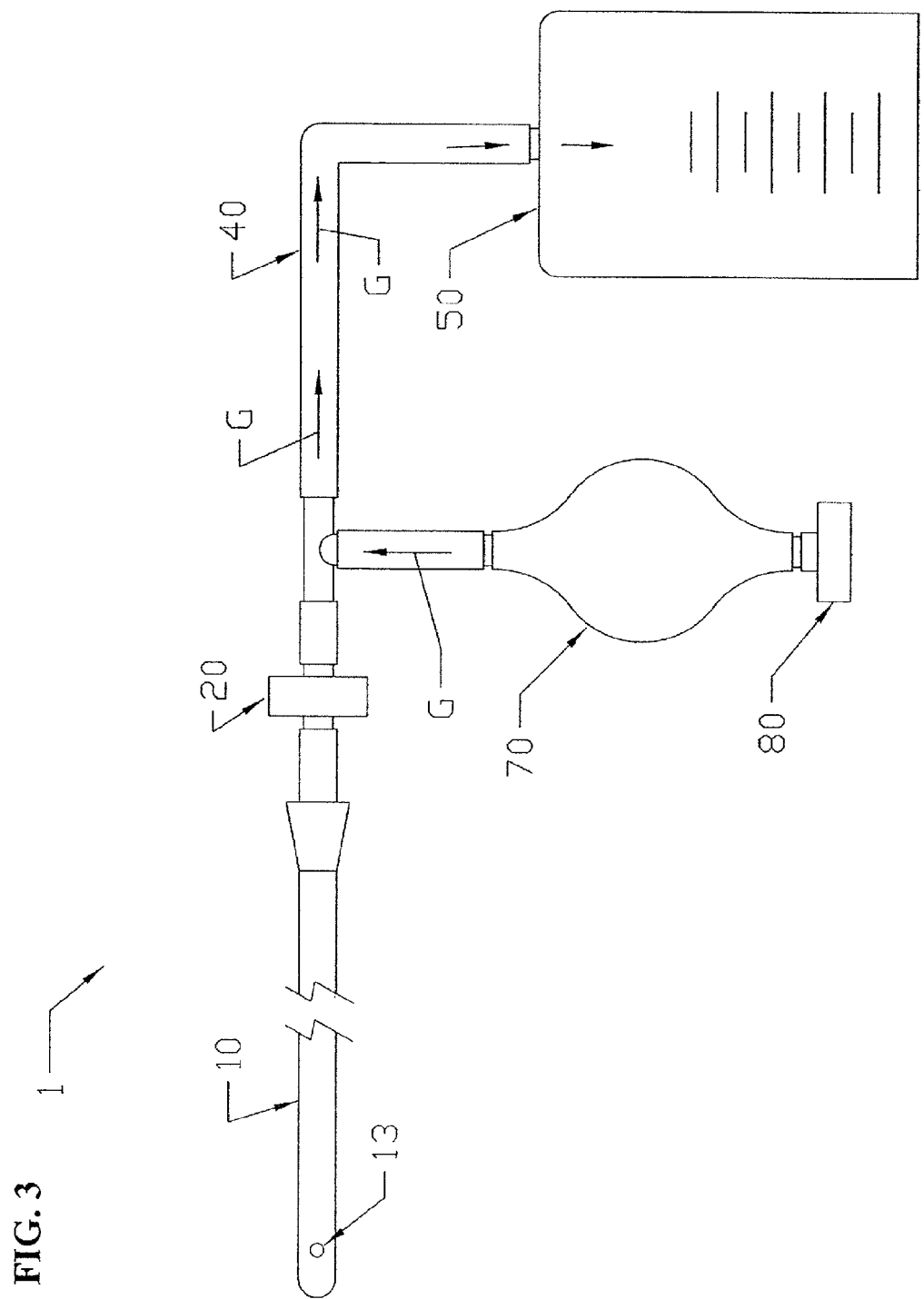
FIG. 3 shows the system of FIG. 1 during a flushing operation mode in accordance with one non-limiting aspect of the invention and shows gas passing out of a gas source, thought the conduit so as to force fluid remaining in the conduit into a collection vessel.

FIGS. 1-3 show a non-limiting embodiment of a catheter draining system 1 in accordance with the present invention. The system 1 utilizes a catheter 10 having a distal end 11 for insertion into, e.g., a bladder, and a proximal end 12 which includes an exit opening allowing a fluid, e.g., urine in a bladder, to pass out of the catheter 10. One or more drainage openings 13 are arranged on the distal end 11 allow fluid to pass into the catheter 10. Any type of catheter, whether known or otherwise, can be utilized provided it functions with the system components of the type described herein.

The system 1 also utilizes a device 20 that allows fluid to pass from the catheter 10 to a collection device 50 which collects the fluid removed with the catheter 10, but which prevents fluid from passing back into the catheter 10. By way of a non-limiting example, the device 20 is a one-way valve. In embodiments, the device 20 can be hydrophobic filter. In embodiments, the device 20 can be a one-way valve of the type disclosed in U.S. Pat. No. 6,240,960 to FILLMORE and/or U.S. Pat. No. 6,481,462 to FILLMORE et al., the disclosures of this document are each expressly incorporated by reference herein in their entireties. In embodiments, the device 20 can have a configuration similar to the sampling coupling device disclosed in U.S. Pat. No. 4,423,741 to LEVY, the disclosure of this document is expressly incorporated by reference herein in its entirety.

The system 1 also utilizes a connection device 30, e.g., a "T" fitting, which has one end coupled to the device 20, another end coupled to a conduit 40 which is in fluid communication with the collection device 50, and another end coupled to a conduit 60 which is in fluid communication with a gas pressure source 70. The conduits 40 and 60 (as well as the conduit sections connecting the catheter 10 to the device 20 and connecting the device 20 to the T fitting 30) can be any type of tubing typically utilized in conventional biological fluid draining systems. The gas pressure device 70 can be a mechanically actuated bulb syringe or other similar device which can produce a pulse of gas pressure sufficient to push gas into the conduit 40 in order to clear or force out any remaining fluid in the conduit 40 and transfer it into the collection device 50. A device 80 coupled to the gas pressure device 70 allows a user to re-inflate the device 80 and to prevent gas from exiting the device 70 except via the conduit 60. By way of a non-limiting example, the gas pressure device 70 can be any type of bulb syringe which is typically utilized in the medical field.

The collection device 50 can be any type of container typically utilized in fluid collection devices. In embodiments, the collection device 50 has indicia which allows a user to accurately measure the amount of fluid inside. In embodiments, one end of the conduit 40 is coupled to a top end portion of the collection device 50 so that fluid entering the collection device 50 will settle at the lowest point and provide for an accurate measurement of the quantity or volume of fluid in the collection device 50.

FIGS. 2 and 3 illustrate one way in which the system of FIG. 1 can be used in the context of draining a bladder. Once the catheter 10 is removed from its package, it can be inserted into the user's body such that the distal end 11 is properly inserted into the bladder. Either before or after, additional system components shown in FIG. 1 are coupled to the catheter 10.

FIG. 2 shows a collection operation mode of the system of FIG. 1 wherein the biological fluid F, i.e., urine, passes (fluid flow movement indicated by arrows) from the catheter 10 through the device 20 and the conduit 40 and into the collection device 50. This draining occurs substantially until the biological fluid stops passing into the collection device 50 and/or for a predetermined amount of time.

FIG. 3 shows a draining or flushing mode of the system of FIG. 1 wherein the gas G passes (gas flow movement indicated by arrows) from the gas pressure source 70 through the conduit 60 and into the conduit 40. This causes a substantial portion (and preferably substantially all) of the biological fluid or liquid remaining in the conduit 40 (at least between the T filling 30 and the collection device 50) after the collection mode to drain (or be flushed) into collection device 50. In the draining or flushing mode, the gas is prevented from passing into the catheter 10 by the device 20. In the embodiment of FIGS. 1-3, the gas pressure is created when a user squeezes the device 70.

Figure 4:
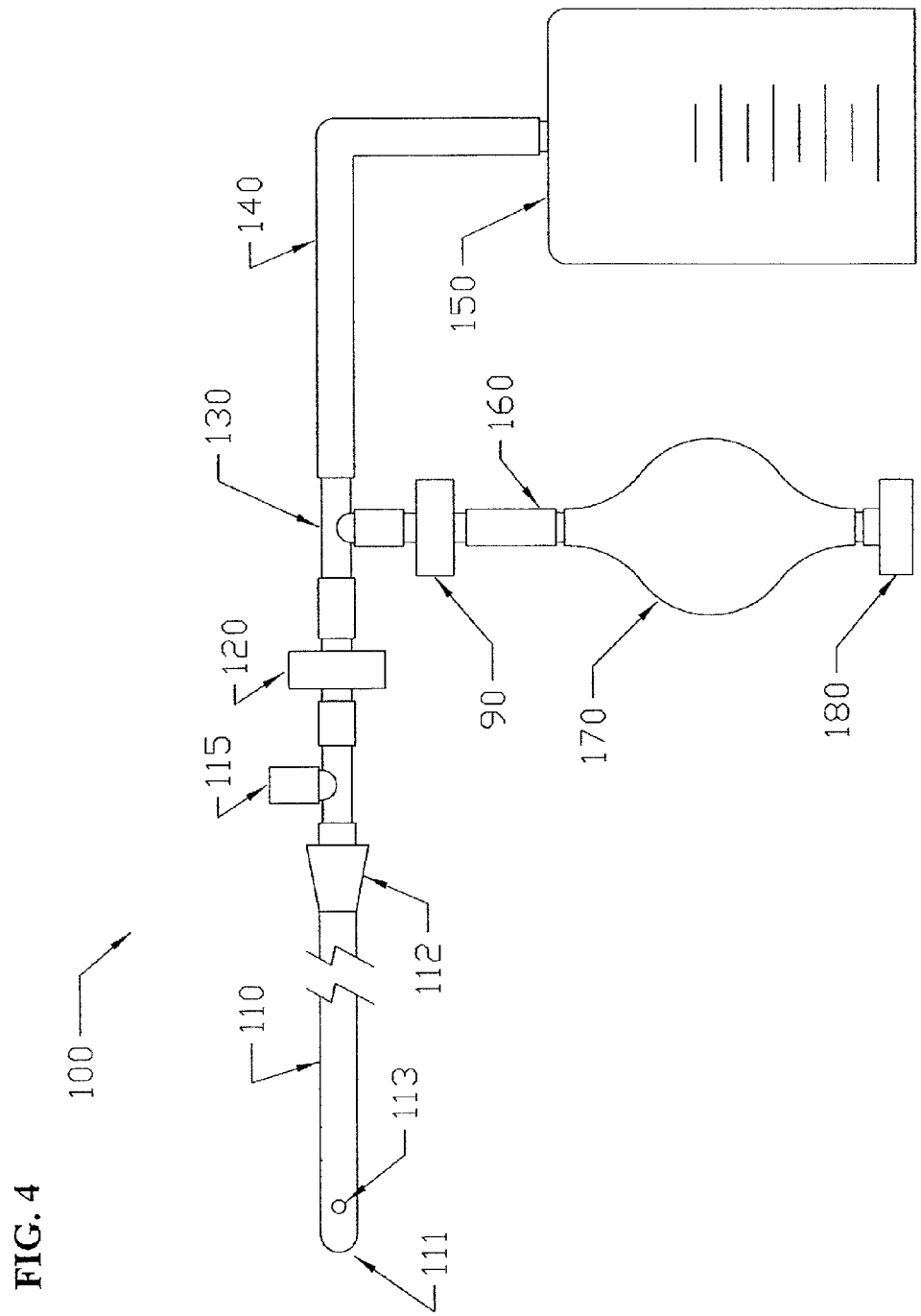
FIG. 4 shows a system for draining and flushing a biological fluid in accordance with another non-limiting embodiment of the invention.

FIG. 4 shows another non-limiting embodiment of a catheter draining system 100 in accordance with the present invention. The system 100 utilizes a catheter 110 having a distal end 111 for insertion into, e.g., a bladder, and a proximal end 112 which includes one or more exit openings allowing a fluid, e.g., urine in a bladder, to pass out of the catheter 110. One or more drainage openings 113 are arranged on the distal end 111 allow fluid to pass into the catheter 110. Any type of catheter, whether known or otherwise, can be utilized provided it functions with the system components of the type described herein.

The system 100 also utilizes a device 120 that allows fluid to pass from the catheter 110 to a collection device 150 which collects the fluid removed with the catheter 110, but which prevents fluid from passing back into the catheter 110. By way of non-limiting example, the device 120 is a one-way valve. In embodiments, the device 120 can be hydrophobic filter. In embodiments, the device 120 can be a one-way valve of the type disclosed in U.S. Pat. No. 6,240,960 to FILLMORE and/or U.S. Pat. No. 6,481,462 to FILLMORE et al., the disclosures of this document are each expressly incorporated by reference herein in their entireties. The system 100 also utilizes a device 115 which allows a user to obtain a sample of the fluid exiting the catheter 110. By way of non-limiting example, the device 115 can have a configuration similar to the sampling coupling device disclosed in U.S. Pat. No. 4,423,741 to LEVY, the disclosure of this document is expressly incorporated by reference herein in its entirety.

The system 100 also utilizes a connection device 130, e.g., a "T" fitting, which has one end coupled to the device 120, another end coupled to a conduit 140 which is in fluid communication with the collection device 150, and another end coupled to a conduit which is in fluid communication with a device 90 that allows gas to pass from the gas pressure source 170 into the conduit 140, but which prevents fluid from passing back into the device 170. By way of non-limiting example, the device 90 is a one-way valve. In embodiments, the device 90 can be hydrophilic filter. The conduits 140 and 160 (as well as the conduit sections connecting the catheter 110 to the devices 115 and 120 connecting the device 120 to the T fitting 130) can be any type of tubing typically utilized in conventional biological fluid draining systems. The gas pressure device 170 can be a mechanically actuated bulb syringe or other similar device which can produce a pulse of gas pressure sufficient to push gas into the conduit 140 in order to clear or force out any remaining fluid in the conduit 140 and transfer it into the collection device 150. A device 180 coupled to the gas pressure device 170 allows a user to re-inflate the device 180 and to prevent gas from exiting the device 170 except via the conduit 160. By way of non-limiting example, the gas pressure device 170 can be any type of bulb syringe which is typically utilized in the medical field.

The collection device 150 can be any type of container typically utilized in fluid collection devices. In embodiments, the collection device 150 has indicia which allows a user to accurately measure the amount of fluid inside. In embodiments, one end of the conduit 140 is coupled to a top end portion of the collection device 150 so that fluid entering the collection device 150 will settle at the lowest point and provide for an accurate measurement of the quantity or volume of fluid in the collection device 150.

The system of FIG. 4 can be used in the context of draining a bladder in the following exemplary manner. Once the catheter 110 is removed from its package, it can be inserted into the user's body such that the distal end 111 is properly inserted into the bladder. Either before or after, additional system components shown in FIG. 4 are coupled to the catheter 110.

In a collection operation mode of the system of FIG. 4, the biological fluid, i.e., urine, passes from the catheter 110 through the devices 115 and 120 and via the conduit 140 and into the collection device 150. This draining occurs substantially until the biological fluid stops passing into the collection device 150 and/or for a predetermined amount of time. If during the collection mode, the user wishes to obtain a sample of the fluid being collected, the user can insert an extraction device, e.g., a syringe, into an access port of the device 115.

In a draining or flushing mode of the system of FIG. 4, gas passes from the gas pressure source 170 through the conduit 160 and device 90 and into the conduit 140. This gas causes a substantial portion (and preferably substantially all) of the biological fluid remaining in the conduit 140 (at least between the T filling 130 and the collection device 150) after the collection mode to drain (or be flushed) into collection device 150. In the draining or flushing mode, the gas is prevented from passing into the catheter 110 by the device 120. In the embodiment of FIG. 4, the gas pressure is created when a user squeezes the device 170.

Figure 5:
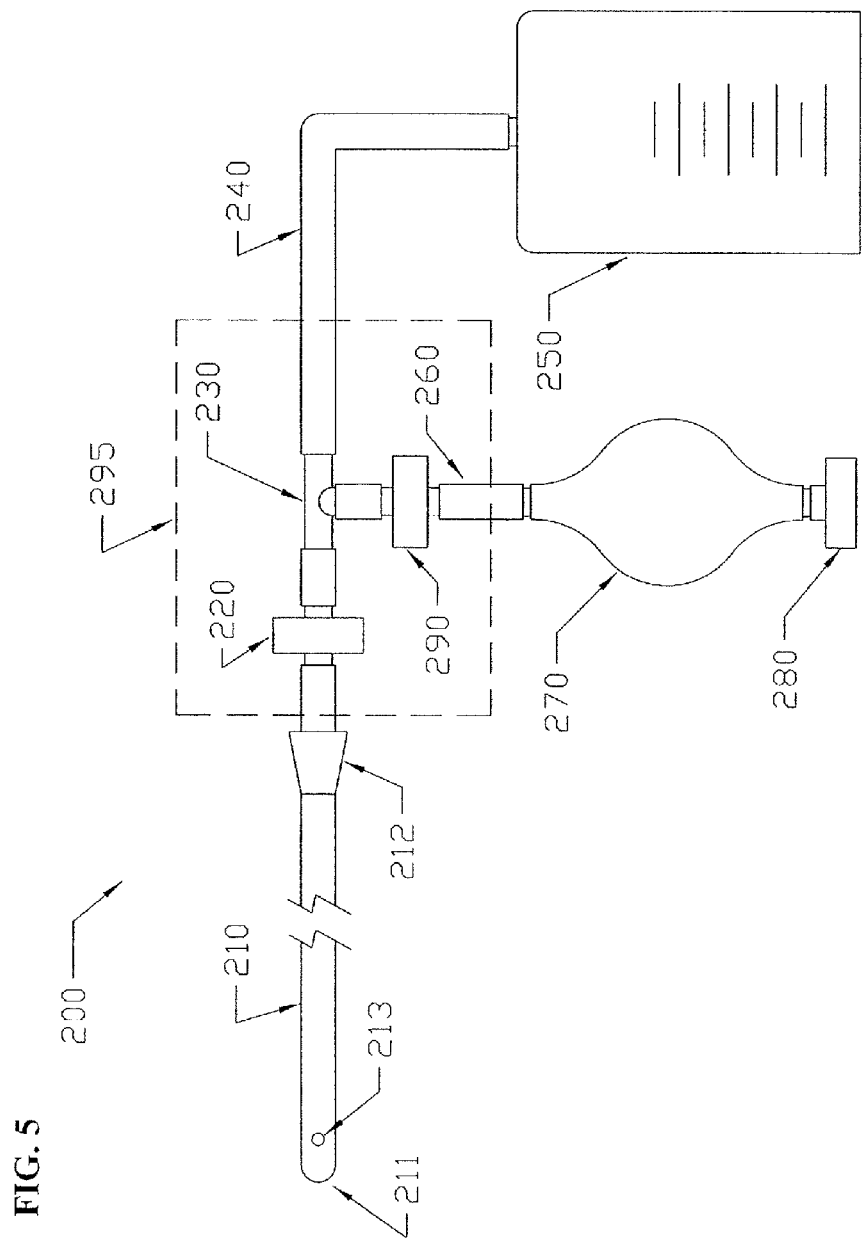
FIG. 5 shows a system for draining and flushing a biological fluid in accordance with still another non-limiting embodiment of the invention.

FIG. 5 shows another non-limiting embodiment of a catheter draining system 200 in accordance with the present invention. The system 200 utilizes a catheter 210 having a distal end 211 for insertion into, e.g., a bladder, and a proximal end 212 which includes an exit opening allowing a fluid, e.g., urine in a bladder, to pass out of the catheter 210. One or more drainage openings 213 are arranged on the distal end 211 allow fluid to pass into the catheter 210. Any type of catheter, whether known or otherwise, can be utilized provided it functions with the system components of the type described herein.

The system 200 also utilizes a device 220 that allows fluid to pass from the catheter 210 to a collection device 250 which collects the fluid removed with the catheter 210, but which prevents fluid from passing back into the catheter 210. By way of non-limiting example, the device 220 is a one-way valve. In embodiments, the device 220 can be hydrophobic filter. In embodiments, the device 220 can be a one-way valve of the type disclosed in U.S. Pat. No. 6,240,960 to FILLMORE and/or U.S. Pat. No. 6,481,462 to FILLMORE et al., the disclosures of this document are each expressly incorporated by reference herein in their entireties. In embodiments, the device 220 can have a configuration similar to the sampling coupling device disclosed in U.S. Pat. No. 4,423,741 to LEVY, the disclosure of this document is expressly incorporated by reference herein in its entirety.

The system 200 also utilizes a connection device 230, e.g., a "T" fitting, which has one end coupled to the device 220, another end coupled to a conduit 240 which is in fluid communication with the collection device 250, and another end coupled to a conduit 260 which is in fluid communication with a gas pressure source 270 via a device 290 which allows gas to flow from the gas pressure device 270 into the conduit 240, but prevents movement of fluid from the conduit 240 into the gas pressure device 270. By way of non-limiting example, the device 290 is a one-way valve. In embodiments, the device 290 can be hydrophilic filter. The conduits 240 and 260 (as well as the conduit sections connecting the catheter 210 to the device 220 and connecting the device 220 to the T fitting 230) can be any type of tubing typically utilized in conventional biological fluid draining systems. The gas pressure device 270 can be a mechanically actuated bulb syringe or other similar device which can produce a pulse of gas pressure sufficient to push gas into the conduit 240 in order to clear or force out any remaining fluid in the conduit 240 and transfer it into the collection device 250. A device 280 coupled to the gas pressure device 270 allows a user to re-inflate the device 280 and to prevent gas from exiting the device 270 except via the conduit 260. By way of non-limiting example, the gas pressure device 270 can be any type of bulb syringe which is typically utilized in the medical field.

In the exemplary embodiment of FIG. 5, at least devices 220, 230 and 290 are arranged in a housing or enclosure 295. The housing 295 is sized and configured to safely store and protect the devices 220, 230 and 290 in a manner which prevents relative movement of these devices. In embodiments, the housing 295 can be made of any medical grade plastic.

The collection device 250 can be any type of container typically utilized in fluid collection devices. In embodiments, the collection device 250 has indicia which allows a user to accurately measure the amount of fluid inside. In embodiments, one end of the conduit 240 is coupled to a top end portion of the collection device 250 so that fluid entering the collection device 250 will settle at the lowest point and provide for an accurate measurement of the quantity or volume of fluid in the collection device 250.

The system of FIG. 5 can be used in the context of draining a bladder in the following exemplary manner. Once the catheter 210 is removed from its package, it can be inserted into the user's body such that the distal end 211 is properly inserted into the bladder. Either before or after, additional system components shown in FIG. 5 are coupled to the catheter 210.

In a collection operation mode of the system of FIG. 5, the biological fluid, i.e., urine, passes from the catheter 210 through the device 220 and via the conduit 240 and into the collection device 250. This draining occurs substantially until the biological fluid stops passing into the collection device 250 and/or for a predetermined amount of time.

In a draining or flushing mode of the system of FIG. 5, gas passes from the gas pressure source 270 through the conduit 260 and device 290 and into the conduit 240. This gas causes a substantial portion (and preferably substantially all) of the biological fluid remaining in the conduit 240 (at least between the T filling 230 and the collection device 250) after the collection mode to drain (or be flushed) into collection device 250. In the draining or flushing mode, the gas is prevented from passing into the catheter 210 by the device 220. In the embodiment of FIG. 5, the gas pressure is created when a user squeezes the device 270.

Figure 6:
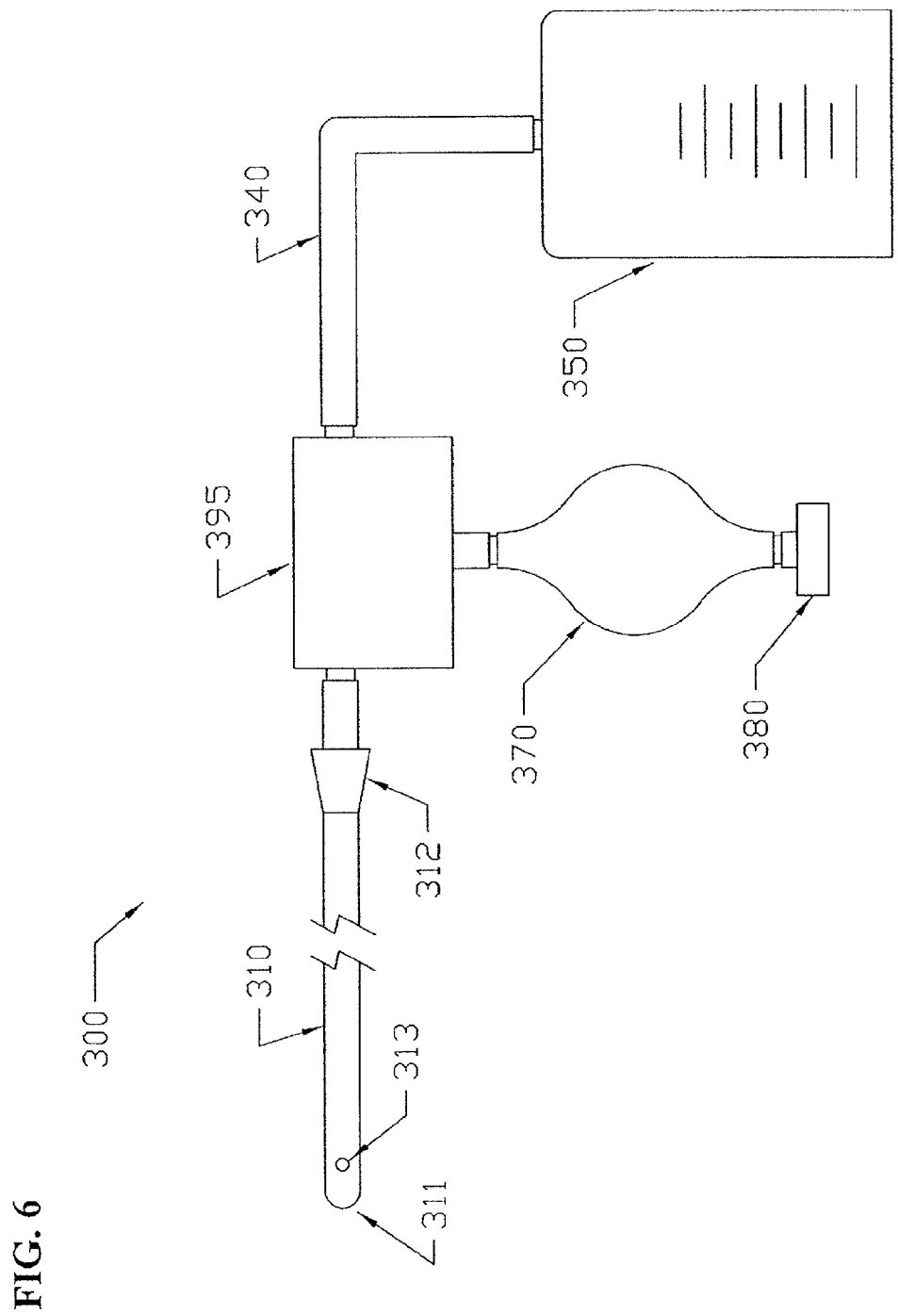
FIG. 6 shows a system for draining and flushing a biological fluid in accordance with still another non-limiting embodiment of the invention.

FIG. 6 shows another non-limiting embodiment of a catheter draining system 300 in accordance with the present invention. The system 300 utilizes a catheter 310 having a distal end 311 for insertion into, e.g., a bladder, and a proximal end 312 which includes an exit opening allowing a fluid, e.g., urine in a bladder, to pass out of the catheter 310. One or more drainage openings 313 are arranged on the distal end 311 allow fluid to pass into the catheter 310. Any type of catheter, whether known or otherwise, can be utilized provided it functions with the system components of the type described herein.

The system 300 also utilizes a fluid control device 395 which includes integrally formed passages and devices which function in the same manner as, e.g., devices 115, 120, 130 and 90 discussed above (see FIG. 4).

The system 300 also utilizes a gas pressure device 370 which can be a mechanically actuated bulb syringe or other similar device which can produce a pulse of gas pressure sufficient to push gas into the conduit 340 in order to clear or force out any remaining fluid in the conduit 340 and transfer it into the collection device 350. A device 380 coupled to the gas pressure device 370 allows a user to re-inflate the device 380 and to prevent gas from exiting the device 370 except via the conduit connecting the gas pressure device 370 to the control device 395. By way of non-limiting example, the gas pressure device 370 can be any type of bulb syringe which is typically utilized in the medical field.

In the exemplary embodiment of FIG. 6, the control device 395 is sized and configured to safely store and protect the devices, e.g., fluid and gas passages, one-way valves, hydrophobic and/or hydrophilic filters, a sampling port, etc., noted above in a manner which allows for automatic activation or operation of the devices. In embodiments, the body of the control 395 can be made of any medical grade plastic.

The collection device 350 can be any type of container typically utilized in fluid collection devices. In embodiments, the collection device 350 has indicia which allows a user to accurately measure the amount of fluid inside. In embodiments, one end of the conduit 340 is coupled to a top end portion of the collection device 350 so that fluid entering the collection device 350 will settle at the lowest point and provide for an accurate measurement of the quantity or volume of fluid in the collection device 350.

The system of FIG. 6 can be used in the context of draining a bladder in the following exemplary manner. Once the catheter 310 is removed from its package, it can be inserted into the user's and/or patient's body such that the distal end 311 is properly inserted into the bladder. Either before or after, additional system components shown in FIG. 6 are coupled to the catheter 310.

In a collection operation mode of the system of FIG. 6, the biological fluid, i.e., urine, passes from the catheter 310 through the device 395 and via the conduit 340 and into the collection device 350. This draining occurs substantially until the biological fluid stops passing into the collection device 350 and/or for a predetermined amount of time.

In a draining or flushing mode of the system of FIG. 6, gas passes from the gas pressure source 370 through the control device 395 and into the conduit 340. This gas causes a substantial portion (and preferably substantially all) of the biological fluid remaining in the conduit 340 (at least between the device 395 and the collection device 350) after the collection mode to drain (or be flushed) into collection device 350. In the draining or flushing mode, the gas is prevented from passing into the catheter 310 by the device 395. In the embodiment of FIG. 6, the gas pressure is created when a user squeezes the device 370.

Figure 7:
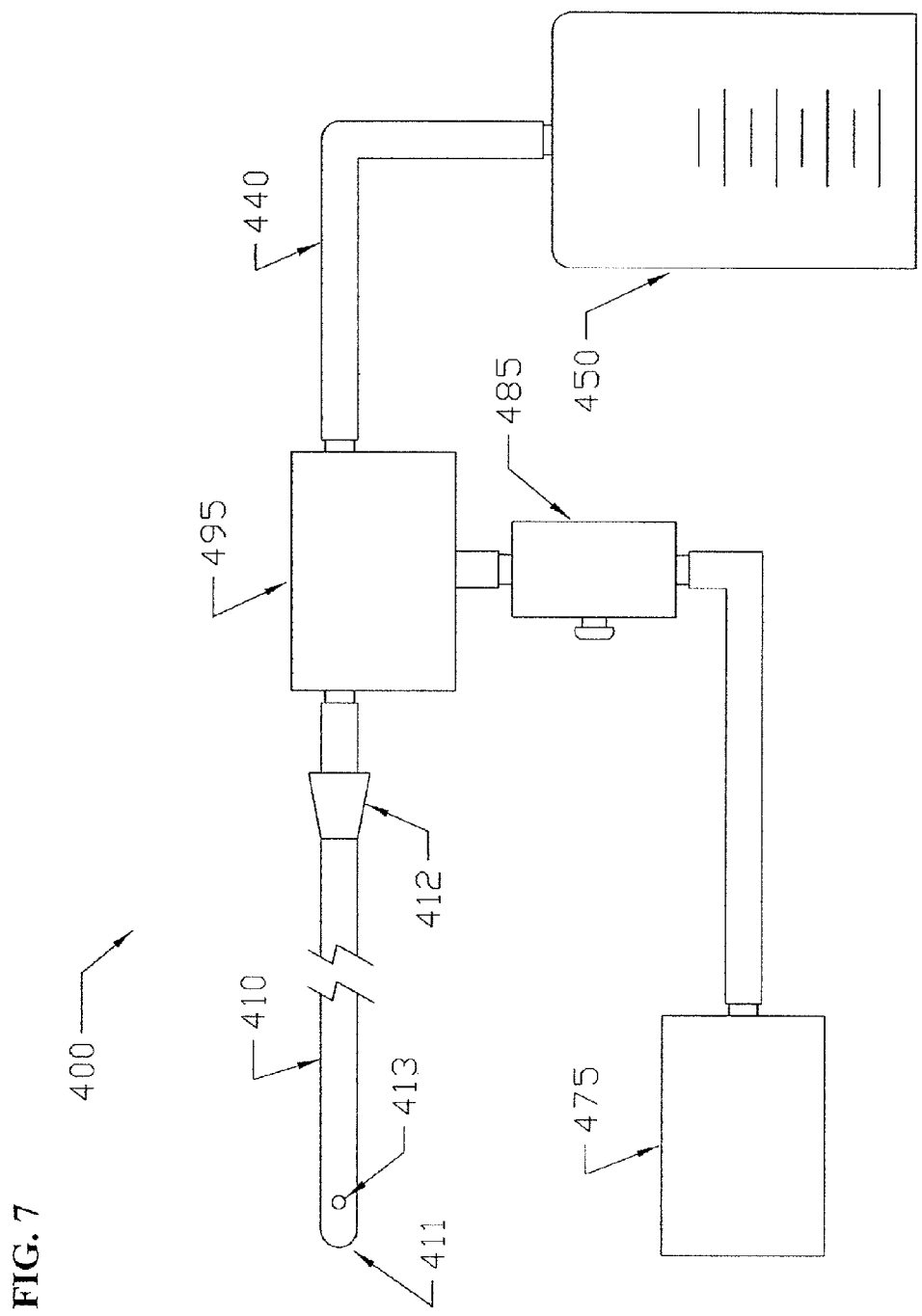
FIG. 7 shows a system for draining and flushing a biological fluid in accordance with still another non-limiting embodiment of the invention.

FIG. 7 shows another non-limiting embodiment of a catheter draining system 400 in accordance with the present invention. The system 400 utilizes a catheter 410 having a distal end 411 for insertion into, e.g., a bladder, and a proximal end 412 which includes an exit opening allowing a fluid, e.g., urine in a bladder, to pass out of the catheter 410. One or more drainage openings 413 are arranged on the distal end 411 allow fluid to pass into the catheter 410. Any type of catheter, whether known or otherwise, can be utilized provided it functions with the system components of the type described herein.

The system 400 also utilizes a fluid control device 495 includes integrally formed passages and devices which function in the same manner as, e.g., devices 115, 120, 130 and 90 discussed above (see FIG. 4).

The system 400 also utilizes a gas supply 475 which can be, e.g., a tank of pressurized gas and/or a gas supply connector arranged on a wall (as typically utilized in a hospital or doctor's office setting). A gas regulating valve or switch 485 is used to regulate or control the amount (and/or pressure) of gas that is allowed to pass into the control device 495. In embodiments, the valve 485 can be a mechanically actuated (whereby, e.g., the user pushes down on a button or trigger to cause gas to pass through the valve 485) and can produce a pulse of gas pressure sufficient to push gas into the conduit 440 in order to clear or force out any remaining fluid in the conduit 440 and transfer it into the collection device 450.

In the exemplary embodiment of FIG. 7, the control device 495 is of the type described above in FIG. 6 and includes, e.g., fluid and gas passages, one-way valves, hydrophobic and/or hydrophilic filters, a sampling port, etc., noted above in a manner which allows for automatic activation or operation of the devices. In embodiments, the body of the control 495 can be made of any medical grade plastic.

The collection device 450 can be any type of container typically utilized in fluid collection devices. In embodiments, the collection device 450 has indicia which allows a user to accurately measure the amount of fluid inside. In embodiments, one end of the conduit 440 is coupled to a top end portion of the collection device 450 so that fluid entering the collection device 450 will settle at the lowest point and provide for an accurate measurement of the quantity or volume of fluid in the collection device 450.

The system of FIG. 7 can be used in the context of draining a bladder in the following exemplary manner. Once the catheter 410 is removed from its package, it can be inserted into the user's body such that the distal end 411 is properly inserted into the bladder. Either before or after, additional system components shown in FIG. 7 are coupled to the catheter 410.

In a collection operation mode of the system of FIG. 7, the biological fluid, i.e., urine, passes from the catheter 410 through the device 495 and via the conduit 440 and into the collection device 450. This draining occurs substantially until the biological fluid stops passing into the collection device 450 and/or for a predetermined amount of time.

In a draining or flushing mode of the system of FIG. 7, gas passes from the gas pressure source 470 through the control device 495 and into the conduit 440. This gas causes a substantial portion (and preferably substantially all) of the biological fluid remaining in the conduit 440 (at least between the device 495 and the collection device 450) after the collection mode to drain (or be flushed) into collection device 450. In the draining or flushing mode, the gas is prevented from passing into the catheter 410 by the device 495. In the embodiment of FIG. 7, the gas pressure is created when a user activates the valve 485.

Figure 8:
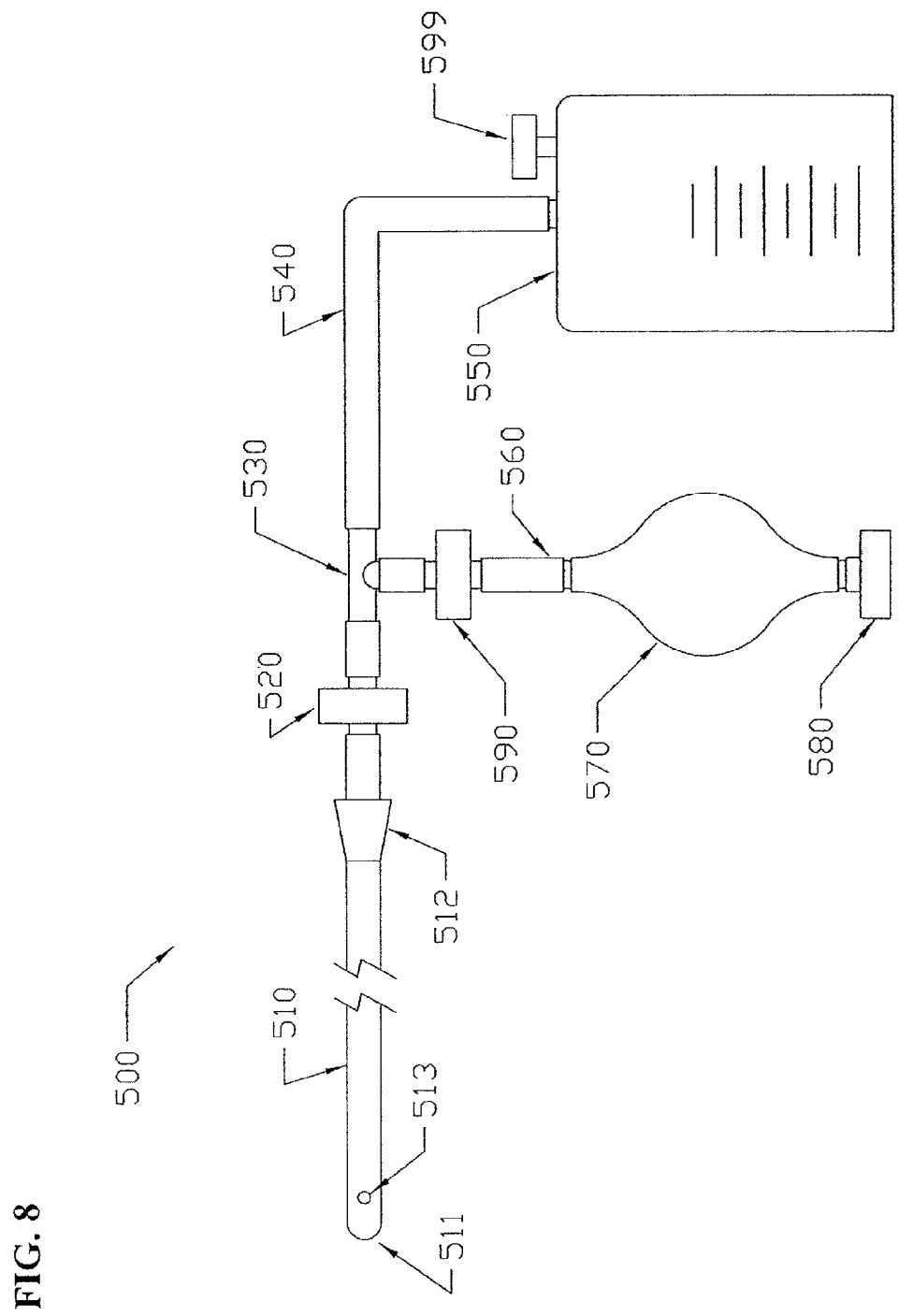
FIG. 8 shows a system for draining and flushing a biological fluid in accordance with still another non-limiting embodiment of the invention.

FIG. 8 shows another non-limiting embodiment of a catheter draining system 500 in accordance with the present invention. The system 500 utilizes a catheter 510 having a distal end 511 for insertion into, e.g., a bladder, and a proximal end 512 which includes an exit opening allowing a fluid, e.g., urine in a bladder, to pass out of the catheter 510. One or more drainage openings 513 are arranged on the distal end 511 allow fluid to pass into the catheter 510. Any type of catheter, whether known or otherwise, can be utilized provided it functions with the system components of the type described herein.

The system 500 also utilizes a device 520 that allows fluid to pass from the catheter 510 to a collection device 550 which collects the fluid removed with the catheter 510, but which prevents fluid from passing back into the catheter 510. By way of non-limiting example, the device 520 is a one-way valve. In embodiments, the device 520 can be hydrophobic filter. In embodiments, the device 520 can be a one-way valve of the type disclosed in U.S. Pat. No. 6,240,960 to FILLMORE and/or U.S. Pat. No. 6,481,462 to FILLMORE et al., the disclosures of this document are each expressly incorporated by reference herein in their entireties. The system 500 can also utilize a device which allows a user to obtain a sample of the fluid exiting the catheter 510. By way of non-limiting example, this device can be incorporated into the device 520 and can have a configuration similar to the sampling coupling device disclosed in U.S. Pat. No. 4,423,741 to LEVY, the disclosure of this document is expressly incorporated by reference herein in its entirety.

The system 500 also utilizes a connection device 530, e.g., a "T" fitting, which has one end coupled to the device 520, another end coupled to a conduit 540 which is in fluid communication with the collection device 550, and another end coupled to a conduit which is in fluid communication with a device 590 that allows gas to pass from the gas pressure source 570 into the conduit 540, but which prevents fluid from passing back into the device 570. By way of non-limiting example, the device 590 is a one-way valve. In embodiments, the device 590 can be hydrophilic filter. The conduits 540 and 560 (as well as the conduit sections connecting the catheter 510 to the device 520 connecting the device 520 to the T fitting 530) can be any type of tubing typically utilized in conventional biological fluid draining systems. The gas pressure device 570 can be a mechanically actuated bulb syringe or other similar device which can produce a pulse of gas pressure sufficient to push gas into the conduit 540 in order to clear or force out any remaining fluid in the conduit 540 and transfer it into the collection device 550. A device 580 coupled to the gas pressure device 570 allows a user to re-inflate the device 580 and to prevent gas from exiting the device 570 except via the conduit 560. By way of non-limiting example, the gas pressure device 570 can be any type of bulb syringe which is typically utilized in the medical field.

The collection device 550 can be any type of container typically utilized in fluid collection devices. In embodiments, the collection device 550 has indicia which allows a user to accurately measure the amount of fluid inside. In embodiments, one end of the conduit 540 is coupled to a top end portion of the collection device 550 so that fluid entering the collection device 550 will settle at the lowest point and provide for an accurate measurement of the quantity or volume of fluid in the collection device 550. A device 599 is arranged on the collection device 550. In embodiments, the device 599 is a vent which allows gas to exit the collection device 550. In embodiments, the device 599 provides an indication that the pressure in the collection device 550 has exceeded a predetermined amount which can provide a visual and/or audible (e.g., providing a whistle sound) indication that the conduit 540 is sufficiently cleared of liquid. In embodiments, the device 599 includes a hydrophilic filter which allows escape of gas and prevents escape of liquid from the collection device 550. In embodiments, the device 599 includes two or more of these features incorporated therein.

The system of FIG. 8 can be used in the context of draining a bladder in the following exemplary manner. Once the catheter 510 is removed from its package, it can be inserted into the user's body such that the distal end 511 is properly inserted into the bladder. Either before or after, additional system components shown in FIG. 8 are coupled to the catheter 510.

In a collection operation mode of the system of FIG. 8, the biological fluid, i.e., urine, passes from the catheter 510 through the device 520 and via the conduit 540 and into the collection device 550. This draining occurs substantially until the biological fluid stops passing into the collection device 550 and/or for a predetermined amount of time. If during the collection mode, the user wishes to obtain a sample of the fluid being collected, the user can insert an extraction device, e.g., a syringe, into an access port of the device 520.

In a draining or flushing mode of the system of FIG. 8, gas passes from the gas pressure source 570 through the conduit 560 and device 590 and into the conduit 540. This gas causes a substantial portion (and preferably substantially all) of the biological fluid remaining in the conduit 540 (at least between the T filling 530 and the collection device 550) after the collection mode to drain (or be flushed) into collection device 550. In the draining or flushing mode, the gas is prevented from passing into the catheter 510 by the device 520. In the embodiment of FIG. 8, the gas pressure is created when a user squeezes the device 570.

Figure 9:
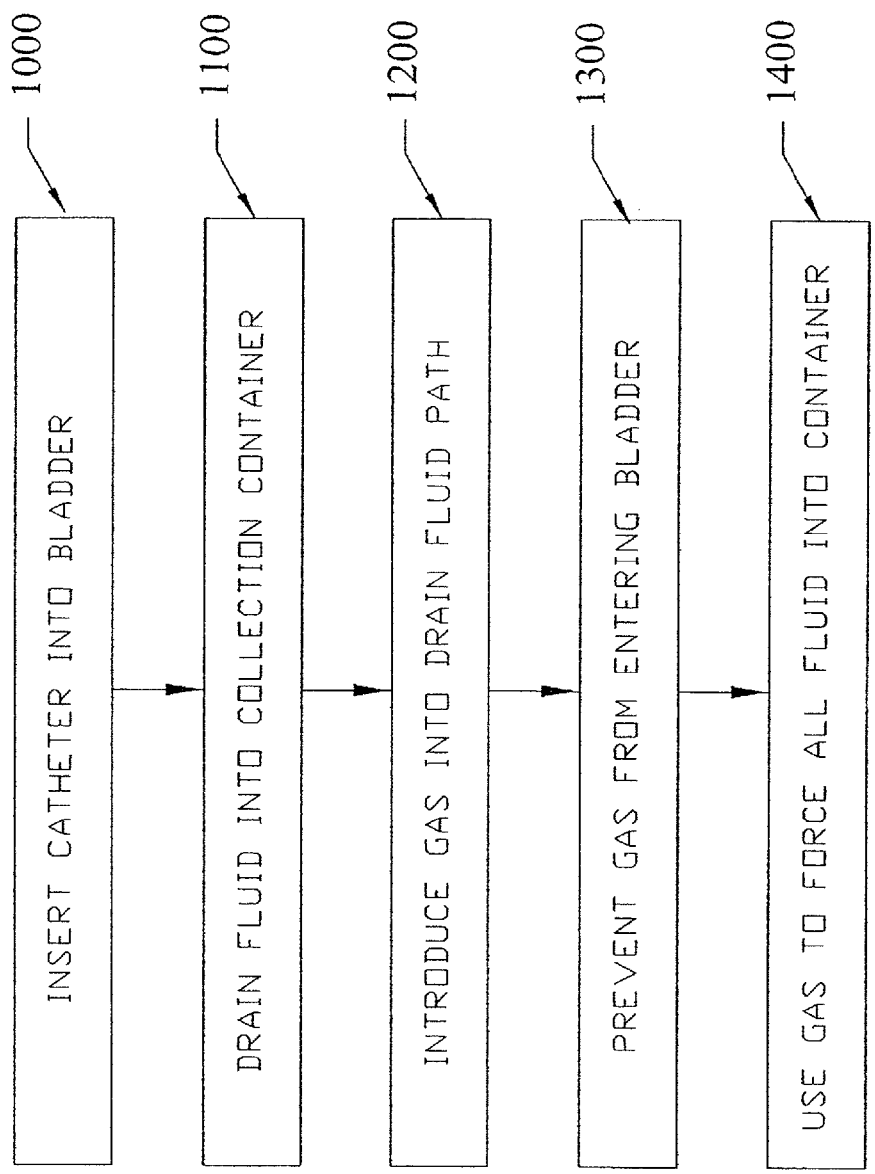
FIG. 9 shows a flow chart identifying steps for practicing a method in accordance with one non-limiting embodiment of the invention.

In embodiments, the invention provides a method of using one or more of the herein disclosed systems which includes, in the exemplary embodiment of FIG. 9, inserting a catheter into a bladder in process stage 1000, draining fluid or liquid into a collection device or container in process stage 1100, introducing gas into a drain fluid path in process stage 1200, prevent gas from entering the bladder in process stage 1300, and use the gas to force all or substantially all of the remaining fluid or liquid in the drain fluid path into the collection device or container in process stage 1400.

Figure 10:
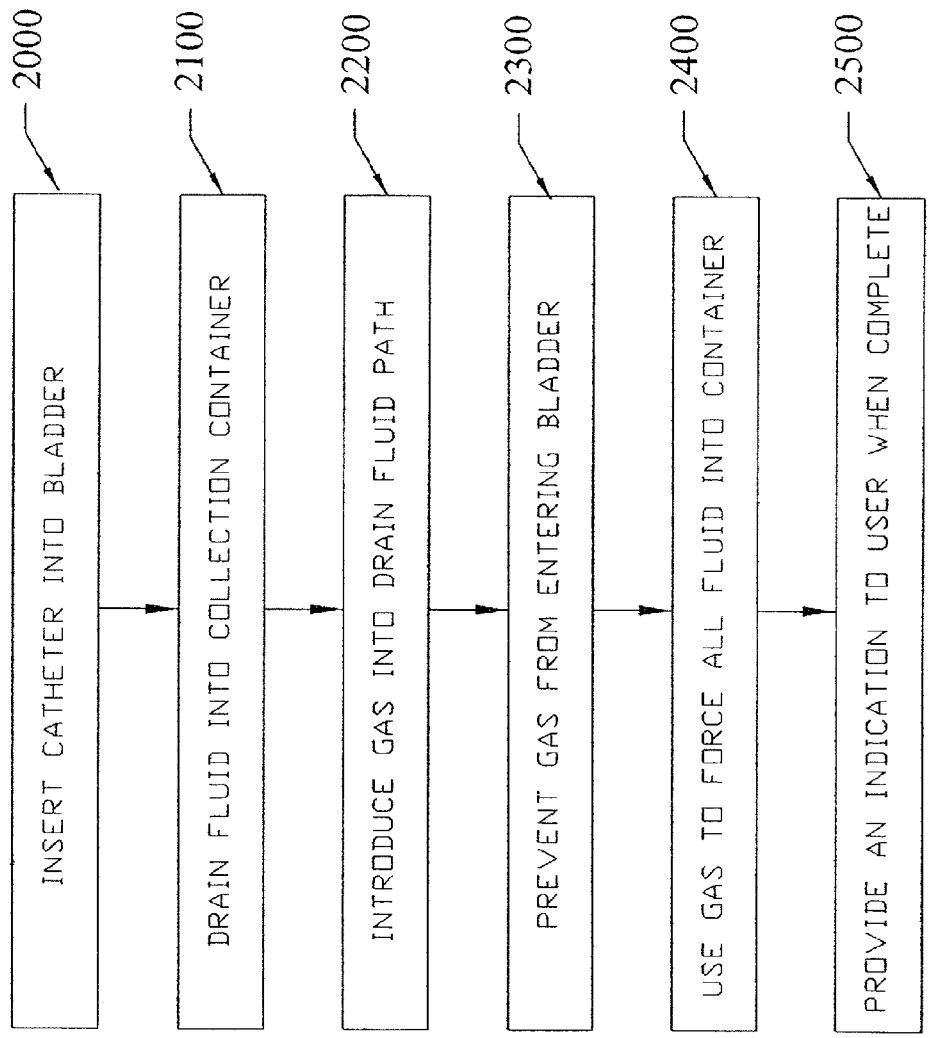
FIG. 10 shows a flow chart identifying steps for practicing a method in accordance with another non-limiting embodiment of the invention.

In embodiments, the invention provides a method of using one or more of the herein disclosed systems which includes, in the exemplary embodiment of FIG. 10, inserting a catheter into a bladder in process stage 2000, draining fluid or liquid into a collection device or container in process stage 2100, introducing gas into a drain fluid path in process stage 2200, prevent gas from entering the bladder in process stage 2300, use the gas to force all or substantially all of the remaining fluid or liquid in the drain fluid path into the collection device or container in process stage 2400, and provide an indication (e.g., visual or audible) to a user that all or substantially all of the liquid in the drain fluid path has been forced into the collection device or container in process stage 2500.

Figure 11:
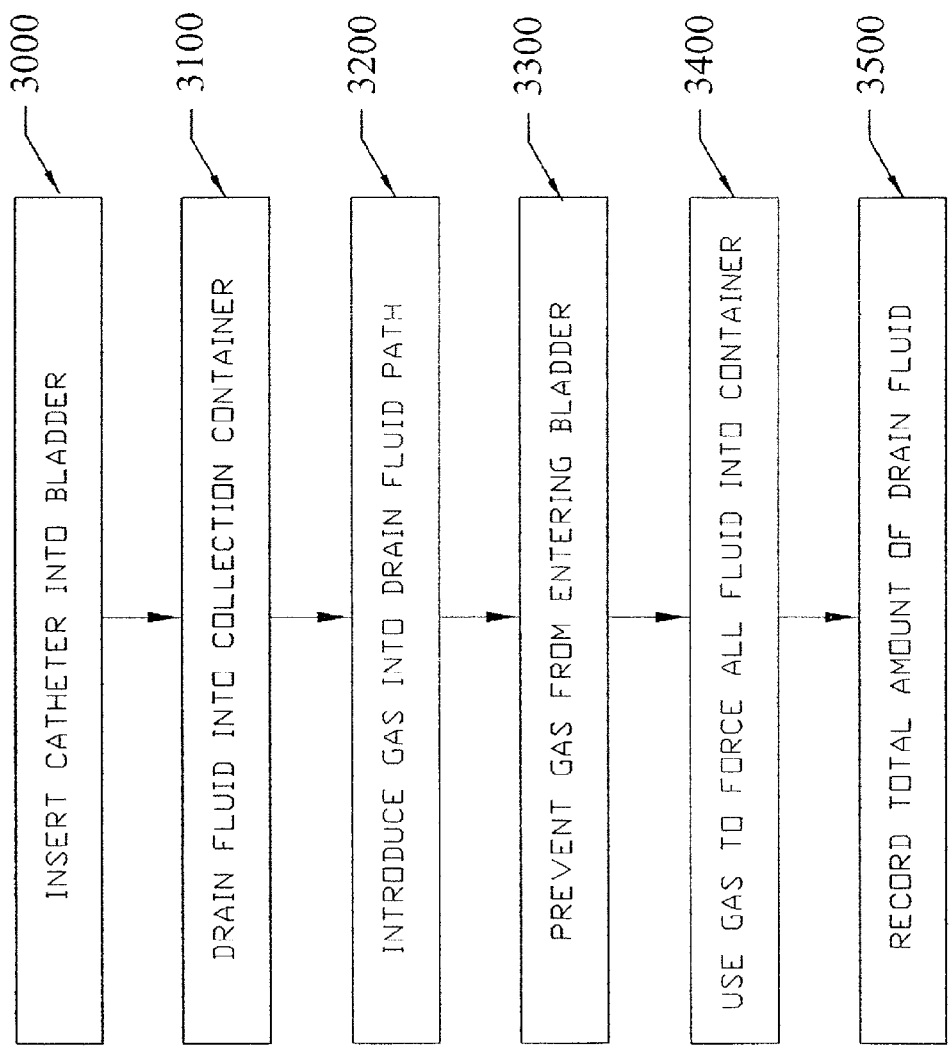
FIG. 11 shows a flow chart identifying steps for practicing a method in accordance with still another non-limiting embodiment of the invention.

In embodiments, the invention provides a method of using one or more of the herein disclosed systems which includes, in the exemplary embodiment of FIG. 11, inserting a catheter into a bladder in process stage 3000, draining fluid or liquid into a collection device or container in process stage 3100, introducing gas into a drain fluid path in process stage 3200, prevent gas from entering the bladder in process stage 3300, use the gas to force all or substantially all of the remaining fluid or liquid in the drain fluid path into the collection device or container in process stage 3400, and record a total amount of the liquid in the collection device or container in process stage 3500.

In each of the herein disclosed embodiments, it is contemplated that features (or process stages) from one embodiment can be used in combination with or can substitute features (or process stages) on another of the disclosed embodiments. Vacuum can also be utilized, e.g., by coupling a vacuum source to the collection device, to assist in removing fluid from the conduit, as is taught in one or more of the prior art documents expressly incorporated by reference herein. In one or more embodiments, the gas can be in the form of a pressure pulse and/or can be continuous gas flow and/or for a predetermined period of time and/or a combination of these. Furthermore, the gas described herein can, in embodiments, be air drawn from the atmosphere immediately surrounding the gas pressure device. Alternatively, the gas can be a gas such as, e.g., nitrogen or oxygen. Other gas can also be utilized provided they function as intended herein.

This invention has been described and specific examples of the invention have been portrayed. While the invention has been described in terms of particular variations and illustrative figures, those of ordinary skill in the art will recognize that the invention is not limited to the variations of figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed:

1. A drainage or collection system for biological fluids, comprising:

a catheter;

a collection device;

at least one conduit connected between the catheter and the collection device and configured for transporting a biological fluid from the catheter to the collection device;

a positive gas pressure source comprising a manually actuated device selected from one of a bulb syringe and a squeeze bulb, the positive gas pressure source configured to feed a gas under positive pressure into the at least one conduit between the catheter and the collection device, a first one-way valve operably attached to the at least one conduit between the positive gas pressure source and the catheter and configured to prevent fluid movement between the positive gas pressure source and the catheter; the first one way valve configured to allow movement of the biological fluid from the catheter to the collection device; and a second one-way valve operably attached to the at least one conduit between the positive gas pressure source and the catheter and configured to prevent movement of the biological fluid between the at least one conduit and the positive gas pressure source; the second one-way valve configured to allow movement of the gas between the positive gas pressure source and the collection device; and wherein the drainage or collection system is configured to use the gas from the positive gas pressure source in the at least one conduit and the first and second one-way valves to drain the biological fluid from the catheter and the at least one conduit into the collection device.

2. The system of claim 1, wherein a pressure of the gas exiting the positive gas pressure source is at least one of:

greater than atmospheric pressure;

greater than atmospheric pressure and having the form of a continuous gas flow;

greater than atmospheric pressure and having the form of a gas flow which occurs for a predetermined amount of time;

greater than atmospheric pressure and having the form of a gas flow which occurs for between about 1 second and about 10 seconds;

greater than atmospheric pressure and having the form of a single pressure pulse; and sufficiently high above atmospheric pressure so as to cause substantially all fluid in the at least one conduit to drain into the collection device.

3. The system of claim 1, further comprising at least one of:

a vacuum configured to be utilized to assist in removal of fluid in the at least one conduit; and a vacuum configured to be utilized to assist in flushing of fluid into the collection device.

4. The system of claim 1, further comprising a device configured for preventing fluid movement between the positive gas pressure source and the catheter.

5. The system of claim 4, wherein the device is a one-way valve coupled to the at least one conduit.

6. The system of claim 4, wherein the device is arranged closer to the catheter than to the collection device.

7. The system of claim 4, wherein the device has one end in fluid communication with the catheter and another end in fluid communication with the collection device.

8. The system of claim 4, wherein the device has one end in fluid communication with the catheter and another end in fluid communication with the positive gas pressure source and the collection device.

9. The system of claim 4, wherein the device further comprises at least one access port configured for removing a sample of the biological fluid passing from the catheter to the collection device.

10. The system of claim 4, further comprising at least one access port configured for removing a sample of the biological fluid at a point upstream of the device.

11. The system of claim 4, further comprising at least one access port coupled to the at least one conduit configured for removing a sample of the biological fluid passing from the catheter and through the at least one conduit.

12. The system of claim 1, wherein the system is configured for the following modes of operation:

a first mode in which the system is configured to allow the biological fluid to pass from the catheter through the at least one conduit and into the collection device; and a second mode in which the system is configured to allow the gas to pass from the positive gas pressure source into the at least one conduit and into the collection device.

13. The system of claim 1, wherein the system is configured for the following modes of operation:

a collection mode in which the system is configured to allow the biological fluid to pass from the catheter through the at least one conduit and into the collection device; and a draining or flushing mode in which the system is configured to allow the gas to pass from the positive gas pressure source into the at least one conduit and to cause a substantial portion of the biological fluid remaining in the at least one conduit after the collection mode to drain into the collection device.

14. The system of claim 1, wherein the system has the following modes of operation:

a collection mode in which the system is configured to allow the biological fluid to pass from the catheter through the at least one conduit and into the collection device substantially until at least one of:

the biological fluid stops passing into the collection device; and at least a predetermined amount of time has expired;

a draining or flushing mode in which the system is configured to allow the gas to pass from the positive gas pressure source into the at least one conduit and to cause a substantial portion of the biological fluid remaining in the at least one conduit after the collection mode to drain into the collection device, wherein, in the draining or flushing mode, the system is configured to prevent the gas from passing into the catheter.

15. The system of claim 1, further comprising a housing configured to at least partially enclose at least one of:

a device configured for preventing fluid movement between the positive gas pressure source and the catheter; and a device configured for preventing fluid movement between the at least one conduit and the positive gas pressure source.

16. The system of claim 1, further comprising a control device having at least two ports in fluid communication with the at least one conduit and containing therein at least one of:

a device configured for preventing fluid movement between the positive gas pressure source and the catheter; and a device configured for preventing fluid movement between the at least one conduit and the positive gas pressure source.

17. The system of claim 16, wherein the control device is configured to have the following mode of operation:

a first mode in which the system is configured to allow the biological fluid to pass from the catheter through the at least one conduit and into the collection device; and a second mode in which the system is configured to prevent the biological fluid from passing from the catheter to the collection device and the gas passes from the positive gas pressure source into the at least one conduit and into the collection device.

18. The system of claim 16, wherein the control device further comprises at least one access port for removing a sample of the biological fluid.

* * * * *